(12) United States Patent
Neimkin et al.

(10) Patent No.: US 12,427,007 B2
(45) Date of Patent: Sep. 30, 2025

(54) MALE URINARY INCONTINENCE DEVICE

(71) Applicant: Dry Ridge Innovations, LLC, Asheville, NC (US)

(72) Inventors: Ronald J. Neimkin, Asheville, NC (US); John J. Smith, III, Winston-Salem, NC (US); Philip M. Allred, III, Kernersville, NC (US); Deborah P. Neimkin, Asheville, NC (US)

(73) Assignee: Dry Ridge Innovations, LLC, Asheville, NC (US)

( * ) Notice: Subject to any disclaimer, the term of this patent is extended or adjusted under 35 U.S.C. 154(b) by 10 days.

(21) Appl. No.: 18/149,337

(22) Filed: Jan. 3, 2023

(65) Prior Publication Data
US 2023/0210649 A1    Jul. 6, 2023

Related U.S. Application Data

(60) Provisional application No. 63/296,058, filed on Jan. 3, 2022.

(51) Int. Cl.
*A61F 2/00* (2006.01)
(52) U.S. Cl.
CPC .... *A61F 2/0054* (2013.01); *A61F 2002/0081* (2013.01); *A61F 2220/0033* (2013.01)
(58) Field of Classification Search
CPC .... A61F 2/0054; A61F 2/0004; A61F 2/0031; A61F 5/48; A61F 5/37; A61F 2005/414; A61F 2005/411; A61F 2005/41; A61F 2005/412; A61F 2005/415; A61F 2005/417; A61F 2005/418; A61F 6/02; A61F 6/04; A61F 6/20-208; A61H 19/50
USPC ......................................................... 128/885
See application file for complete search history.

(56) References Cited

U.S. PATENT DOCUMENTS

| | | | |
|---|---|---|---|
| 4,537,313 A | 8/1985 | Workman | |
| 4,800,900 A | 1/1989 | French | |
| 5,263,947 A | 11/1993 | Kay | |
| 5,415,179 A | 5/1995 | Mendoza | |
| 5,526,803 A * | 6/1996 | Kelly | A61F 5/41 128/95.1 |
| 6,289,895 B1 | 9/2001 | Cheng et al. | |
| 6,904,916 B2 | 6/2005 | Bakane | |
| 7,166,092 B2 | 1/2007 | Elson et al. | |
| 2020/0030135 A1 | 1/2020 | Woodyard | |

\* cited by examiner

*Primary Examiner* — Michelle J Lee
*Assistant Examiner* — Robin Han
(74) *Attorney, Agent, or Firm* — Coffield Heedy Kilgore PLLC; William Heedy

(57) ABSTRACT

A male urinary incontinence device includes a circumferential band including a securing end, an elongated portion, and a receiving end, the circumferential band including a plurality of securing protuberances and the receiving end including a receiving aperture having an outer diameter, an inner diameter, and an inner aperture; a ventral base including a ventral base aperture and a plurality of protuberances located on the exterior and interior surface of the ventral base; a dorsal base including a lower dorsal bar, a dorsal base aperture, and at least one lateral dorsal flange with the at least one lateral dorsal flange having at least one lateral flange notch.

14 Claims, 23 Drawing Sheets

MALE URINARY INCONTINENCE DEVICE

RELATED APPLICATIONS

This application claims priority to and incorporates entirely by reference U.S. Provisional Application Ser. No. 63/296,058, filed on Jan. 3, 2022.

FIELD OF THE INVENTION

This invention relates to a male urinary incontinence device and, more particularly, to a male urinary incontinence device including a circumferential band, ventral base, and dorsal base. The male urinary incontinence device provides mechanical pressure against the urethra to inhibit urinary flow. The male urinary incontinence device is further capable of providing urethral pressure without obstructing continued blood flow.

BACKGROUND OF THE INVENTION

Male urinary incontinence is a condition in men resulting from the loss of bladder control, often resulting in occasional urinary leakage or involuntary urination. Such incontinence may include stress incontinence, urge incontinence, overflow incontinence, functional incontinence, or a mixture of these incontinence types. Although urinary incontinence can occur as a result of aging, it can also result from specific underlying medical conditions, eating and drinking habits, physical problems, and in connection with some types of prostate surgery. The condition may be temporary or permanent.

In certain cases, male urinary incontinence can be managed with lifestyle or dietary changes. In circumstances where lifestyle or dietary changes are not corrective, male urinary incontinence may, in some cases, be managed by surgical procedures, implantable devices, pharmaceuticals, or catheters. These solutions, however, are often ineffective, unsuitable, or undesirable for many men. For example, surgical procedures and implantable devices can be overly invasive or unavailable to certain patients, with the possibility of unwanted side effects. Pharmaceutical solutions may have unwanted side effects or may also be unavailable to certain patients. Similarly, catheters are often an inconvenient or temporary solution, requiring frequent emptying of a reservoir bag and often proving untenable or undesirable for many men.

Another potential option is the use of incontinence pads and/or disposable undergarments. These devices, however, come with numerous drawbacks and undesirable characteristics, including a stigma that many people associate with the use of these products. Additionally, the use of incontinence pads and undergarments can have undesirable consequences, such as skin irritation or unwanted odor, and these options may prove undesirable for long-term use.

Because of these drawbacks, a convenient and less-invasive means for managing male urinary incontinence is via mechanical means. Such mechanical devices function by applying pressure to the urethra sufficient to close the urethral tube at a specific position, thus preventing urinary leakage. These mechanical devices are known by several terms but are often referred to as male incontinence clamps.

Existing incontinence clamps contain numerous deficiencies that prevent continuous, long-term adoption. One of the foremost drawbacks of existing incontinence clamps is their inability to function effectively and comfortably with no undesirable ancillary effects. This is particularly true where the incontinence clamp is to be worn for extended periods of time.

Specifically, many users find incontinence clamps to be uncomfortable, and even painful, and are unable to wear them. These incontinence clamps are unable to provide urethral pressure without exerting excessive pressure along the arteries and veins located in the dorsal region of the penis, thus constricting blood flow through the penis.

The urethra is surrounded by a column of spongy tissue known as the corpus spongiosum, located in the ventral portion of the penis. Blood flow is supplied to the penis by several arteries and veins located on the dorsum of the penis and commonly referred to specifically as dorsal arteries and dorsal veins.

Because of this anatomical configuration, one aim of the present invention is to provide mechanical pressure to the urethra, sufficient to preclude flow through the urethra while maintaining blood flow through the dorsal arteries and veins. Many existing devices are not adapted to accommodate the relative mechanical forces necessary for an effective and comfortable fit, but rather are limited to applying uniform bidirectional pressure that precludes urinary flow while also inhibiting blood flow, thus proving uncomfortable for long-term extended use.

Existing clamp devices also prove difficult to properly position for efficacy and comfort, and similarly, these existing devices lack a suitable fit, leading the device to shift and reposition during use. This lack of a proper fit adversely affects the efficacy and comfort of these devices.

Similarly, many existing incontinence clamps utilize fabric components in attempts to alleviate concerns with comfort and efficacy. A secondary, undesirable effect of such materials is their moisture absorbing properties, leading to skin irritation and bacterial and/or fungal growth. Because of these properties, these types of urinary clamps require frequent cleaning, sanitizing, and/or replacement of the clamp, thus proving time consuming, inconvenient, and costly.

Existing incontinence clamps are further unsuitable for long-term use because of the inability to regularly and properly clean the device. Many of these incontinence clamps contain complicated multi-component assemblies that are difficult to disassemble for thorough cleaning and sanitization. Similarly, many devices are constructed from materials that are not capable of thorough cleaning and sanitization.

Therefore, there exists a need for a male urinary incontinence device that is effective at managing urinary incontinence while being comfortable, durable, and easy to clean. Specifically, a device is needed for providing localized pressure sufficient to preclude urethral flow and a proper fit to prevent shifting or repositioning of the device during use. Similarly, such device must also provide relative pressure that assures a proper fit while not precluding blood flow through the dorsal arteries and veins.

SUMMARY OF THE INVENTION

In accordance with one form of this invention, there is provided a male urinary incontinence device for use in inhibiting urinary flow through the urethra, the male urinary incontinence device including a circumferential band including a securing end, an elongated portion, and a receiving end, the circumferential band including a plurality of securing protuberances and the receiving end including a receiving aperture having an outer diameter, an inner diameter, and an inner aperture; a dorsal base including a dorsal base aperture and a plurality of protuberances located on the exterior and interior surface of the dorsal base; a ventral base including a lower ventral bar, a ventral base aperture, and at least one lateral ventral flange with the at least one lateral ventral flange having at least one lateral flange notch.

BRIEF DESCRIPTION OF THE DRAWINGS

For a fuller understanding of the nature of the present invention, reference should be made to the following detailed description, taken in conjunction with the accompanying drawings in which.

Like reference numerals refer to like reference parts throughout the several views of the drawings.

DETAILED DESCRIPTION

Figure 1:
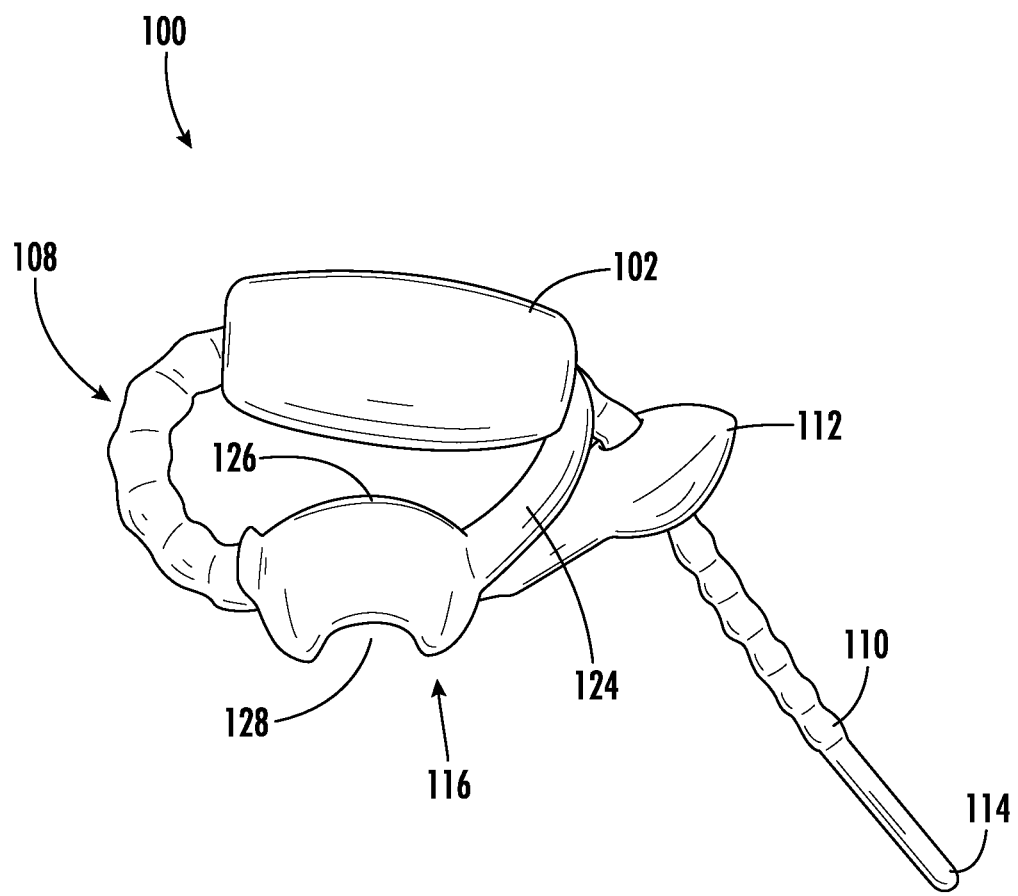
FIG. 1 is a front view of a male urinary incontinence device, in accordance with one embodiment.
Figure 2:
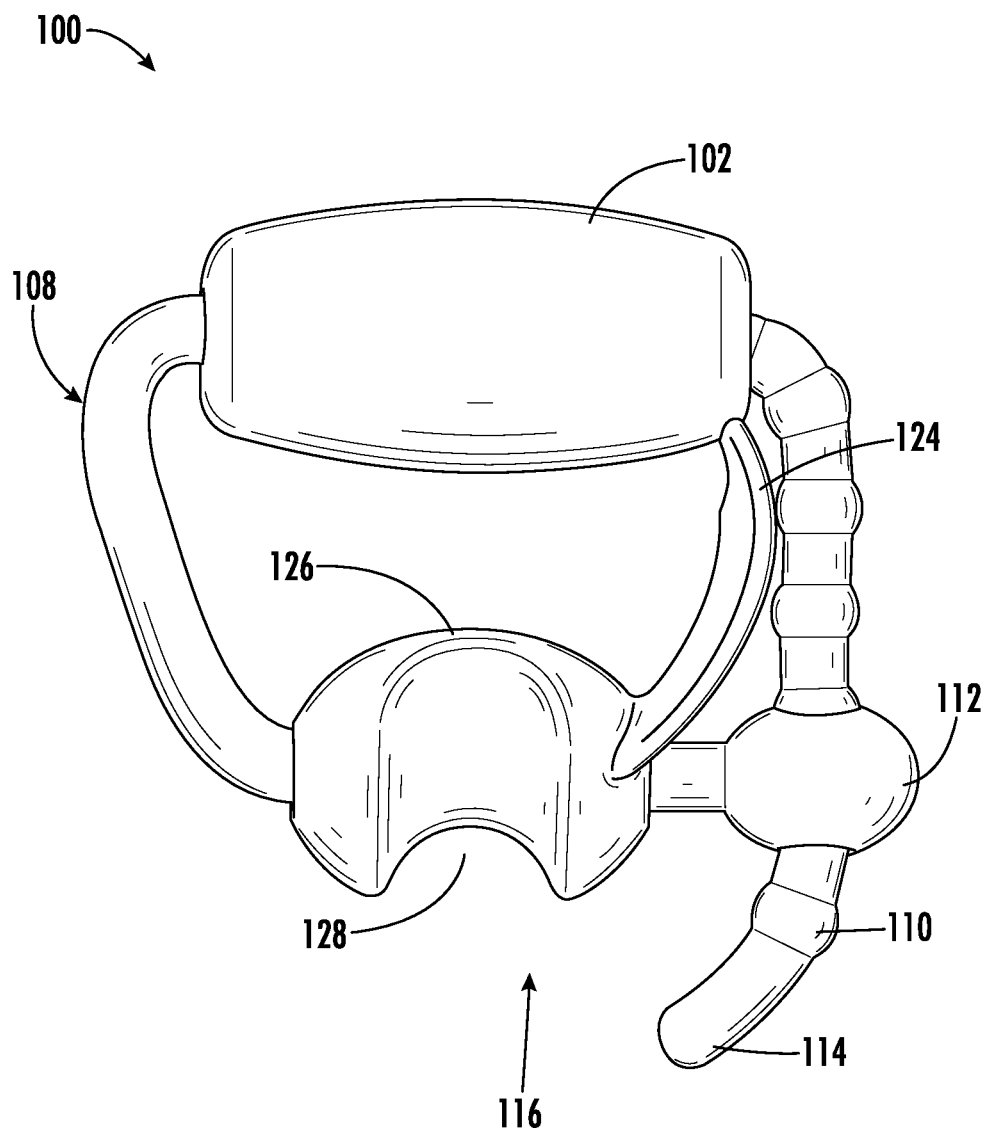
FIG. 2 is a front view of a male urinary incontinence device, in accordance with one embodiment.

Referring to the several views of the drawings, the male urinary incontinence device 100 is shown and described herein.

Referring initially to FIGS. 1, 2, and 9-12, the male urinary incontinence device 100 is designed to be secured around the penis, proximal to the base of the penis.

The male urinary incontinence device 100 includes a circumferential band 108 having a securing end 114 and a receiving end 112. The receiving end 112 includes a receiving aperture 118, which includes an outer diameter 120 and an inner aperture 122.

Figure 3:
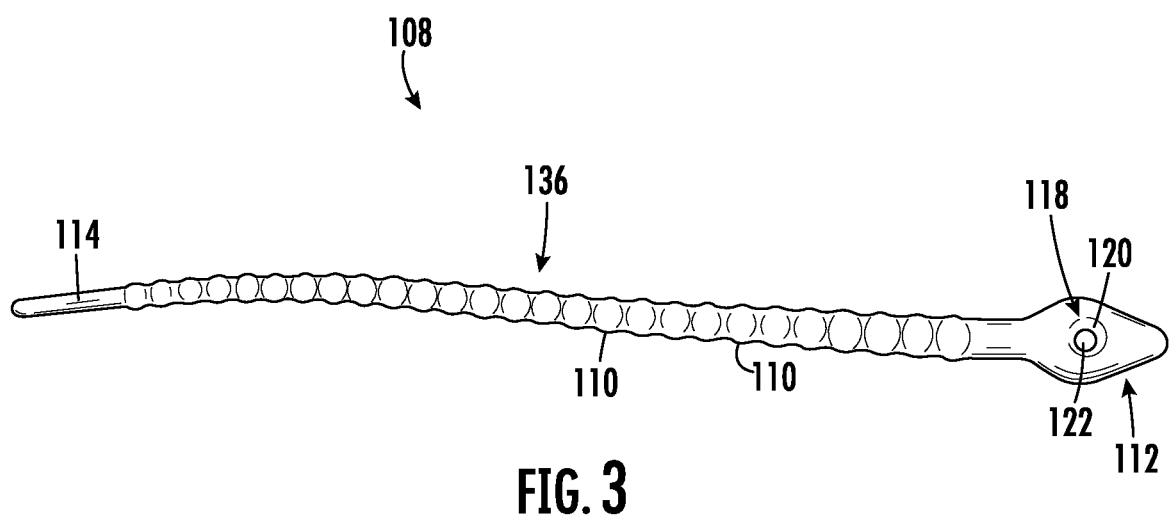
FIG. 3 is a profile view of the circumferential band of a male urinary incontinence device, in accordance with one embodiment.

Referring now to FIG. 3, the circumferential band 108 includes an elongated portion 136 located between the securing end 114 and the receiving end 112. The elongated portion 136 includes a plurality of securing protuberances 110 extending outwards from and circumferentially around the elongated portion 136.

The securing end 114 is sized for receipt through the inner aperture 122 of the receiving end 112. The securing end 114 may be further moved through the inner aperture 122 to allow the securing protuberances 110 to pass through the inner aperture 122. The securing protuberances 110 are sized circumferentially to be larger than the inner aperture 122 so that the securing end 114 is secured through the receiving end 112 of the circumferential band 108. It will be appreciated that the securing protuberances 110 may be configured in various numbers and at various spacing intervals along the elongated portion 136, thus allowing finer tightening adjustment of the male urinary incontinence device 100.

The circumferential band 108 may be composed of a flexible material such as silicone, a plastic polymer, or similar durable, resilient, nonporous material that is capable of being sterilized or sanitized.

Figure 4:
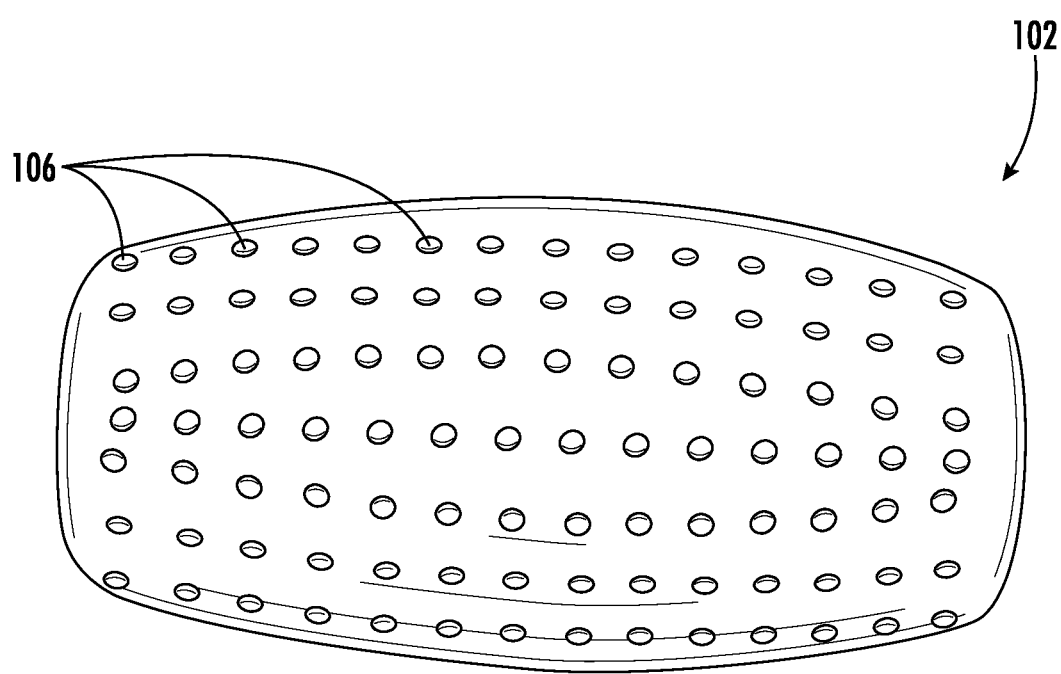
FIG. 4 is a front view of the dorsal base of a male urinary incontinence device, in accordance with one embodiment.
Figure 5:
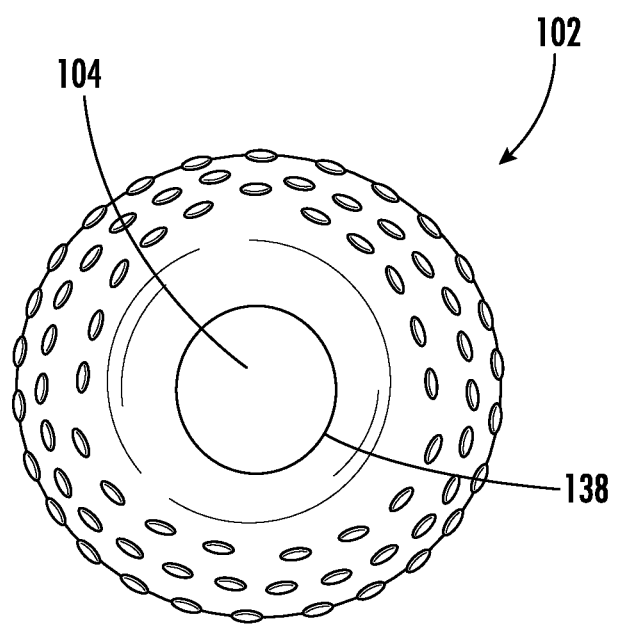
FIG. 5 is a profile view of the dorsal base of a male urinary incontinence device, in accordance with one embodiment.

As seen in FIGS. 4 and 5, in one embodiment, the dorsal base 102 may be an elongated body including a dorsal base aperture 104 and a plurality of dorsal base protuberances 106.

The dorsal base protuberances 106 may be located on all or a portion of the exterior surface of the dorsal base 102. The dorsal base 102 may be oriented around the circumferential band 108 such that the dorsal base protuberances 106 face inward providing a frictional contact surface sufficient to maintain the male urinary incontinence device's 100 position on the user. It will be appreciated by one of ordinary skill in the art that the number, size, and/or positioning of the dorsal base protuberances 106 may be varied to achieve the desired level of friction without compromising the comfort of the male urinary incontinence device 100.

In one embodiment, the dorsal base aperture 104 is sized at a diameter equal to the cross-sectional diameter of the securing protuberances 110 to allow the dorsal base 102 to be frictionally secured against the securing protuberances 110, thus inhibiting the dorsal base 102 from shifting or moving relative to its position on the circumferential band 108.

In another embodiment, the dorsal base aperture 104 is sized at a diameter smaller than the cross-sectional diameter of the securing protuberances 110 to allow the dorsal base 102 to be frictionally secured against the securing protuberances 110, thus inhibiting the dorsal base 102 from shifting or moving relative to its position on the circumferential band 108.

The interior surface of the dorsal base aperture 104 may also contain a plurality of dorsal base aperture protuberances 138 to provide a frictional contact surface against the elongated portion 136 of the circumferential band 108, thus inhibiting the dorsal base 102 from shifting or moving relative to its position on the circumferential band 108.

It will be appreciated by one of ordinary skill in the art that the dorsal base 102 may be composed of one or more materials of varying densities to allow for appropriate pressure to be applied on the penis opposite the urethra and corpus spongiosum while maintaining proper blood flow through the dorsal region of the penis and providing a level of comfort to the user. Similarly, the density of the dorsal base 102 provides sufficient deformation to allow the securing protuberances 110 to pass through the dorsal base aperture 104.

Figure 6:
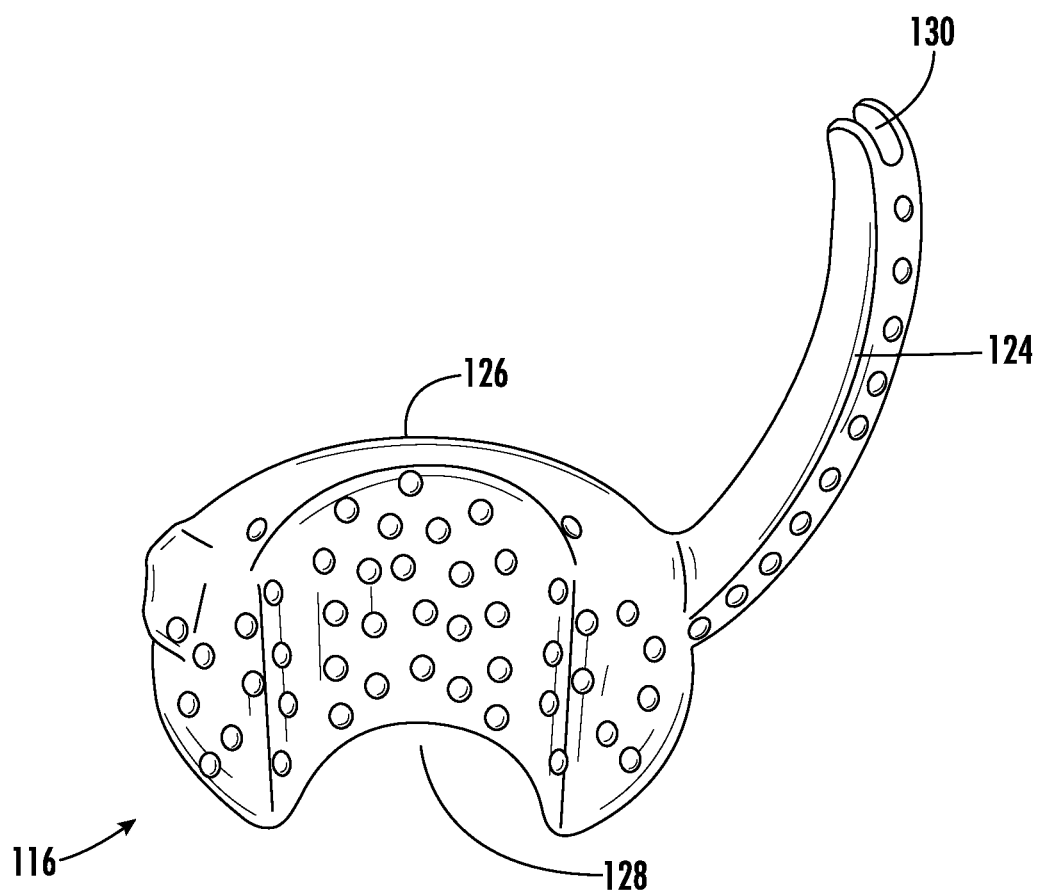
FIG. 6 is a front view of the ventral base of a male urinary incontinence device, in accordance with one embodiment.
Figure 7:
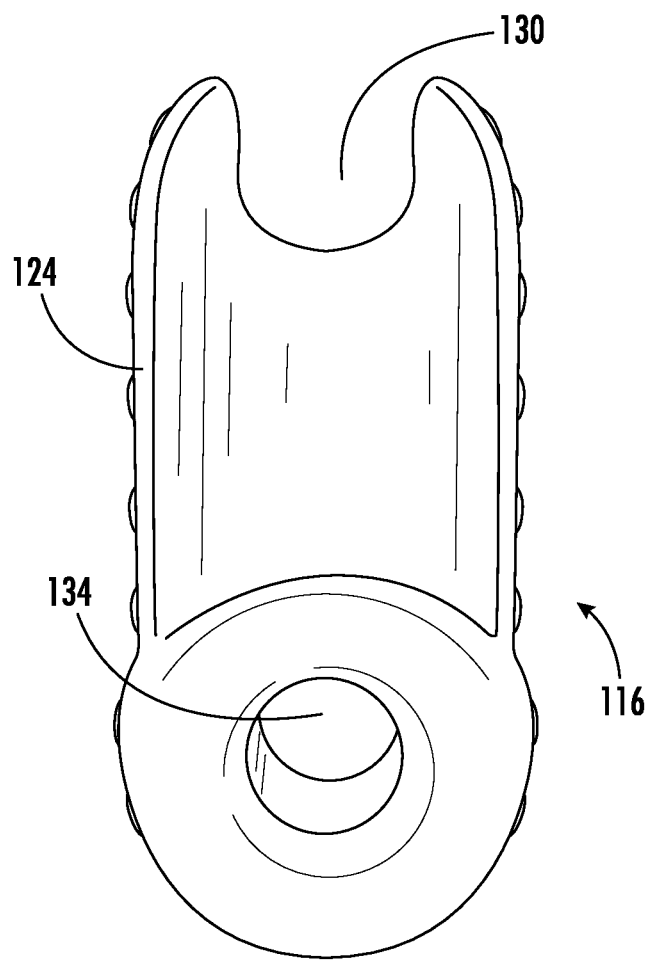
FIG. 7 is a profile view of the ventral base of a male urinary incontinence device, in accordance with one embodiment.
Figure 8:
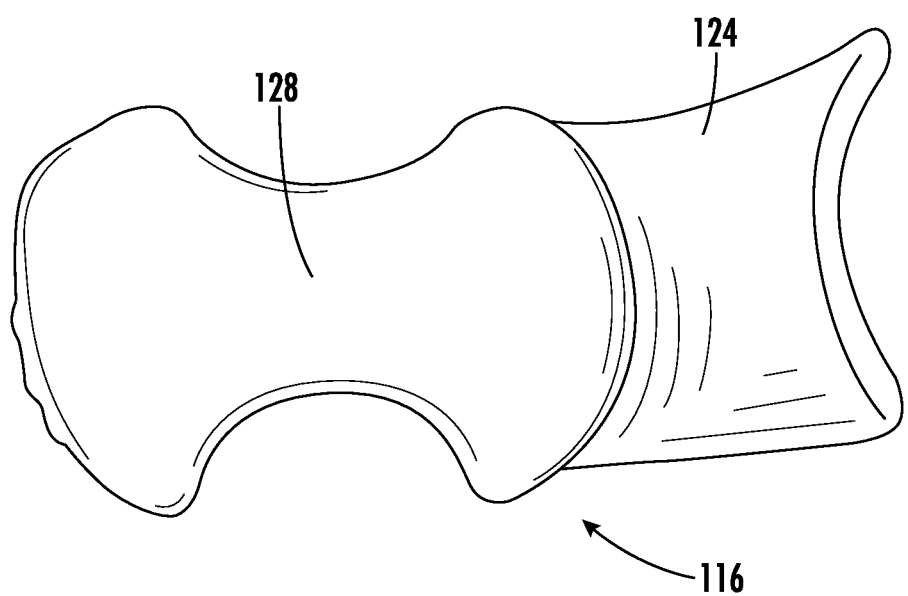
FIG. 8 is a top view of the ventral base of a male urinary incontinence device, in accordance with one embodiment.
Figure 9:
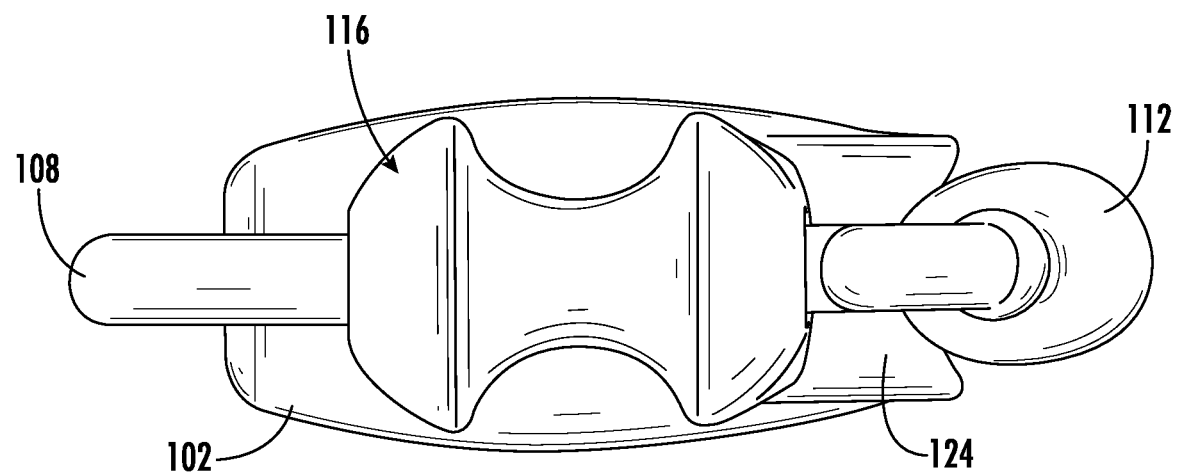
FIG. 9 is a bottom view of a male urinary incontinence device, in accordance with one embodiment.
Figure 10:
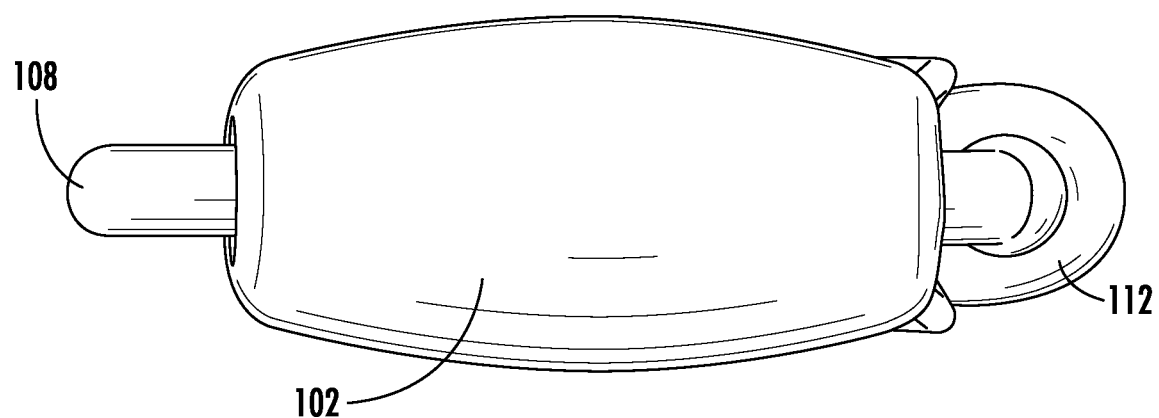
FIG. 10 is a top view of a male urinary incontinence device, in accordance with one embodiment.
Figure 11:
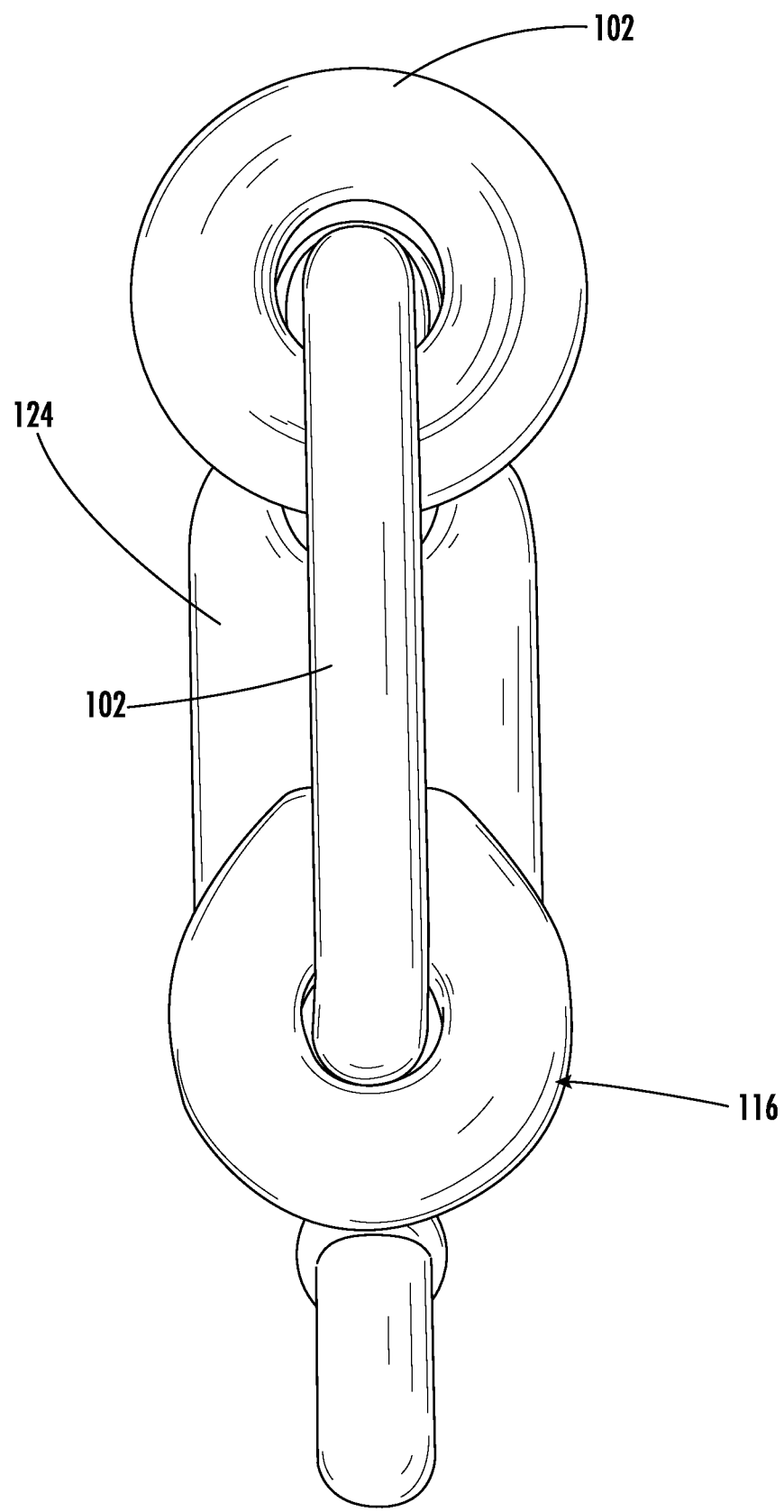
FIG. 11 is a profile view of a male urinary incontinence device, in accordance with one embodiment.
Figure 12:
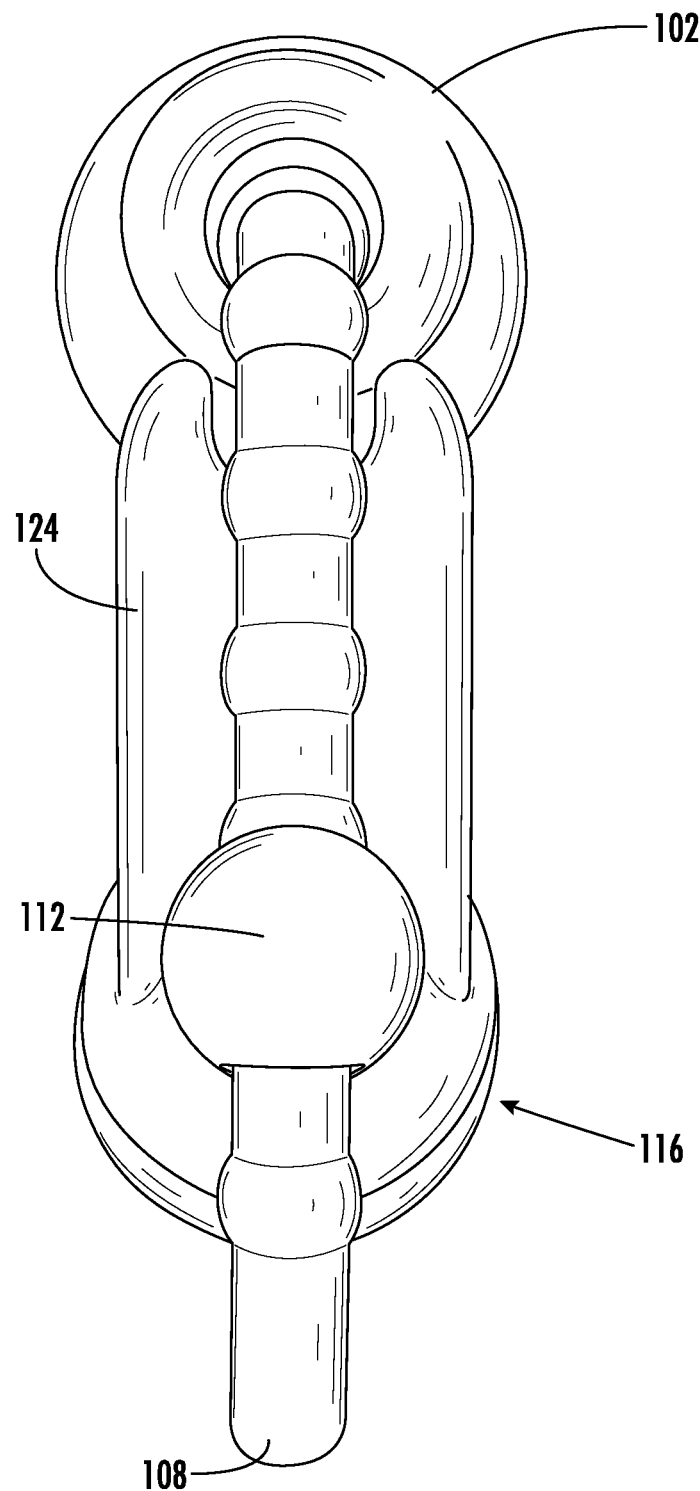
FIG. 12 is a profile view of a male urinary incontinence device, in accordance with one embodiment.

Referring now to FIGS. 6-8, in one embodiment the ventral base 116 may include a ventral bar 126, one or more lateral ventral flanges 124, one or more lateral flange notches 130, and a ventral base aperture 134.

According to one embodiment, the ventral base aperture 134 is sized at a diameter equal to the cross-sectional diameter of the securing protuberances 110 to allow the ventral base 116 to be frictionally secured against the securing protuberances 110, thus inhibiting the ventral base 116 from shifting or moving relative to its position on the circumferential band 108.

According to one embodiment, the ventral base aperture 134 is sized at a diameter smaller than the cross-sectional diameter of the securing protuberances 110 to allow the ventral base 116 to be frictionally secured against the securing protuberances 110, thus inhibiting the ventral base 116 from shifting or moving relative to its position on the circumferential band 108.

It will be appreciated by one of ordinary skill in the art that the ventral base 116 may be composed of one or more materials of varying densities to allow for appropriate pressure to be specifically applied to the urethra and corpus spongiosum, thus preventing urinary flow through the urethra when the device is properly worn, while maintaining proper blood flow through the penis. Similarly, the density of the materials included in the ventral base 116 may provide sufficient deformation to allow the securing protuberances 110 to pass through the ventral base aperture 134 while maintaining sufficient contact to inhibit the ventral base 116 from shifting or moving relative to its position on the circumferential band 108.

According to one embodiment, the ventral base 116 includes one or more lateral ventral flanges 124 sized and configured to be seated around the circumference of a penis, although it is not necessary that the lateral ventral flanges 124 fully contacts the penis. The exterior surfaces of the lateral ventral flange 124 include a concave curvature sized for seating of the circumferential band 108. It will be appreciated by one of ordinary skill in the art that the male urinary incontinence device 100 may have a second lateral ventral flange 124 located at the opposite lateral side of the ventral base 116 without departing from the spirit and scope of the present invention. Such a second lateral ventral flange 124 may provide a more appropriate fit depending on the specific application.

As shown in, for example, FIGS. 1, 3, and 9-12, the ventral base 116 is located such that the lateral ventral flange 124 is adjacent to or on the same side as the receiving end 112 of the circumferential band 108 when the male urinary incontinence device 100 is assembled. This location of the lateral ventral flange 124 optimizes the ease by which a user may position and tighten the male urinary incontinence device 100 around the penis.

Similarly, the lateral ventral flange 124 includes a lateral flange notch 130 that includes a concave space sized to be seated around at least a portion of the circumference of the elongated portion 136 of the circumferential band 108.

According to one embodiment, a user attaches the male urinary incontinence device 100 around the circumference of the user's penis, with the dorsal base 102 being oriented against the dorsal side of the penis and the ventral base 116 being oriented against the ventral side of the penis. The user may insert the securing end 114 of the circumferential band 108 through the receiving aperture 118 of the receiving end 112 of the circumferential band 108. The user may continue to feed the securing end 114 through the receiving aperture 118 to thus tighten the male urinary incontinence device 100 around the user's penis, where the larger circumference of the securing protuberances 110 inhibit movement of the securing end 114 and elongated portion 136 relative to the smaller circumference of the receiving aperture 118.

Figure 13:
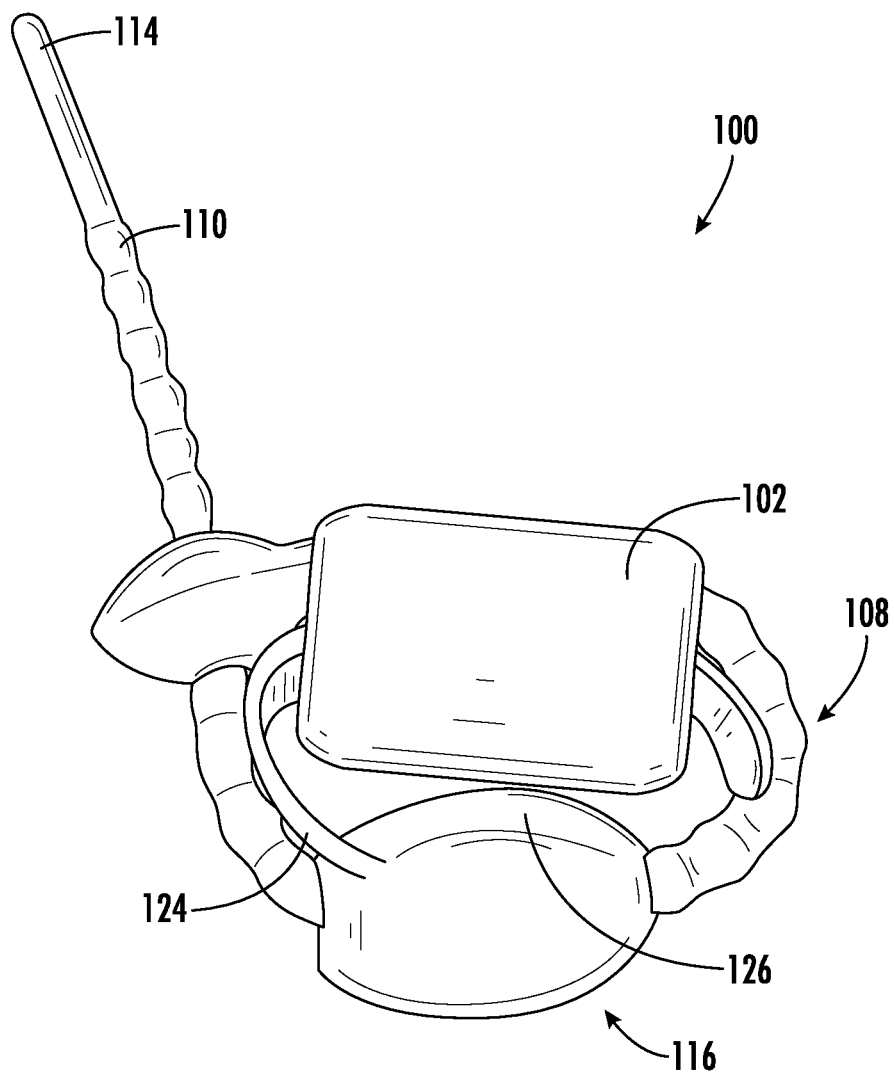
FIG. 13 is a front view of a male urinary incontinence device, in accordance with one embodiment.

Referring now to FIGS. 13-23, in one embodiment, the dorsal base 102 includes a dorsal base aperture 104 and a dorsal base receiver 140 sized for receipt of the lateral ventral flange 124 of the ventral base 116. For example, by facilitating the lateral ventral flange's 124 insertion into the dorsal base receiver 140, a user may effectively adjust the male urinary incontinence device 100 while also allowing for increased stability where the lateral ventral flange 124 is secured in the dorsal base receiver 140. According to different embodiments, and as shown in FIG. 13, the lateral ventral flange 124 may be of varying lengths to facilitate its insertion into and through the dorsal base receiver 140 of the dorsal base 102. For example, the lateral ventral flange 124 may be inserted at varying depths into the dorsal base receiver 140 to allow a user to adjust the positioning and tightness of the dorsal base 102, ventral base 116, and lateral ventral flange 124, thereby allowing the user to effectively customize the fit of the male urinary incontinence device 100. The lateral ventral flange 124 may be of such a sufficient length that it may be inserted into one end of the dorsal base receiver 140 and emerge from the opposing end of the dorsal base receiver 140.

According to this embodiment, the external surface of the lateral ventral flange 124 may include a concave curvature sized for seating of the circumferential band 108, and the lateral ventral flange 124 may similarly be sized and configured to be seated partially around the circumference of a user's penis, although it is not necessary that the lateral ventral flange 124 fully contacts the penis. The exterior surface of the lateral It will be further appreciated by one of ordinary skill in the art that the ventral base 116 may include two lateral ventral flanges 124, each extending in opposite directions from the ventral bar 126, wherein the dorsal base receiver 140 may be sized for receipt of the two lateral ventral flanges 124 simultaneously, or alternatively, the dorsal base 102 may include two dorsal base receivers 140, each for respective receipt of one of the dorsal base receivers 140. Such a second lateral ventral flange 124 may provide a more appropriate fit depending on the specific application.

As shown in FIG. 13, there is an engaged configuration by which a user may attach the male urinary incontinence device 100 around the circumference of the user's penis, with the dorsal base 102 being oriented against the dorsal side of the penis and the ventral base 116 being oriented against the ventral side of the penis. The user may insert the securing end 114 of the circumferential band 108 through the receiving aperture 118 of the receiving end 112 of the circumferential band 108, and the lateral ventral flange 124 may be inserted through the dorsal base receiver 140 of the dorsal base 102. The user may continue to feed the securing end 114 of the circumferential band 108 through the receiving aperture 118 to thus tighten the male urinary incontinence device 100 around the user's penis, where the larger circumference of the securing protuberances 110 inhibit movement of the securing end 114 and elongated portion 136 relative to the smaller circumference of the receiving aperture 118. Similarly, the user may continue feeding the lateral ventral flange 124 through the dorsal base receiver 140 to further secure and tighten the male urinary incontinence device 100 around the user's penis.

Figure 14:
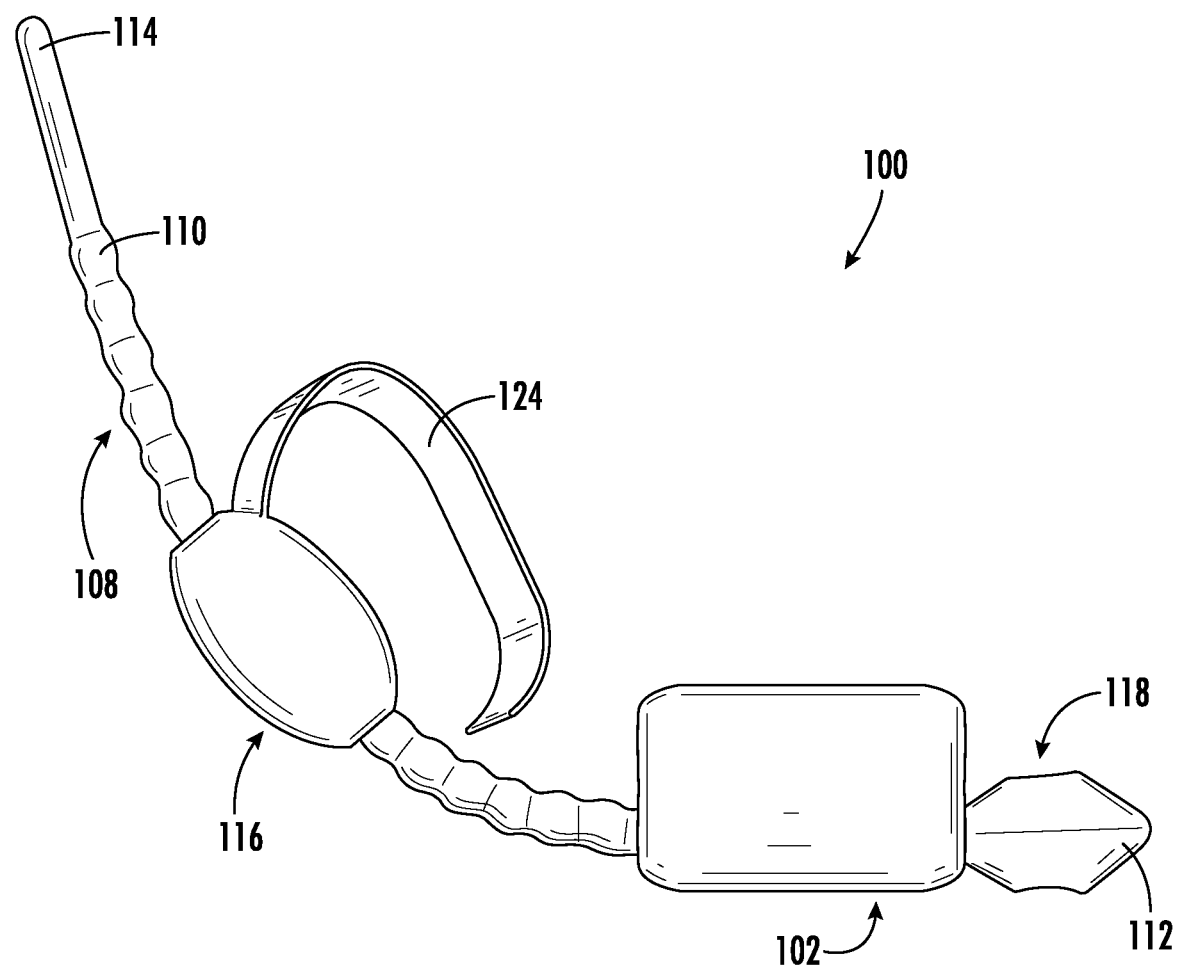
FIG. 14 is a front view of a male urinary incontinence device in a disengaged state, in accordance with one embodiment.
Figure 15:
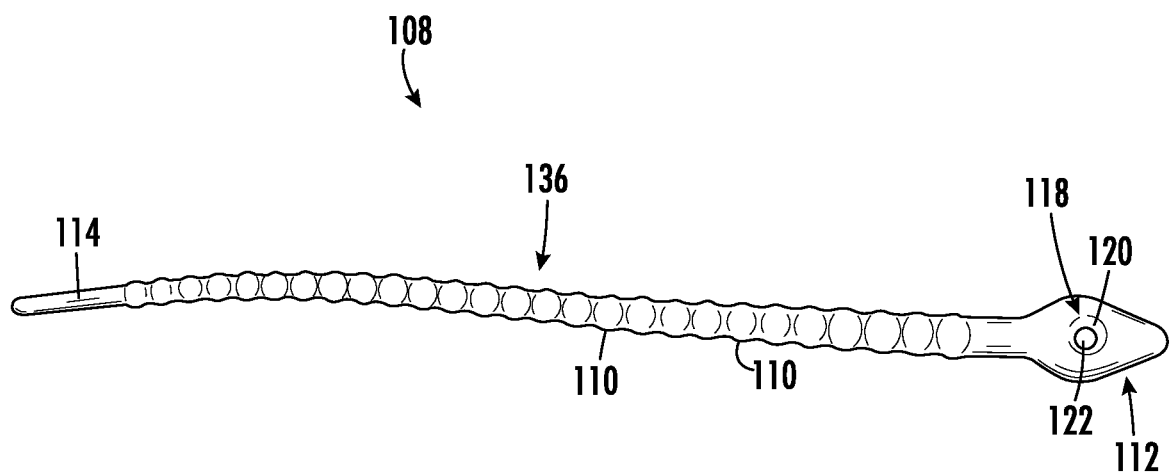
FIG. 15 is a profile view of the circumferential band of a male urinary incontinence device, in accordance with one embodiment.

As shown in FIG. 14, the male urinary incontinence device 100 may be transitioned to a disengaged configuration wherein the securing end 114 of the circumferential band 108 is removed from the receiving aperture 118 of the receiving end 112 of the circumferential band. The lateral ventral flange 124 may similarly be removed from the dorsal base receiver 140 of the dorsal base 102. In this disengaged configuration, the user may thus remove the ventral base 116 and dorsal base 102 from the circumferential band 108 for cleaning, repair, or replacement of components.

As shown in FIG. 13, the ventral base 116 may lack the lower ventral notch 128 without departing from the spirit or scope of the invention. Similarly, as shown in FIGS. 13-14, the dorsal base 102 may be located immediately adjacent to the receiving end 112 of the circumferential band 108, such that the ventral base 116 is located between the dorsal base 102 and the securing end 114 on the elongated portion 136 of the circumferential band 108.

Figure 17:
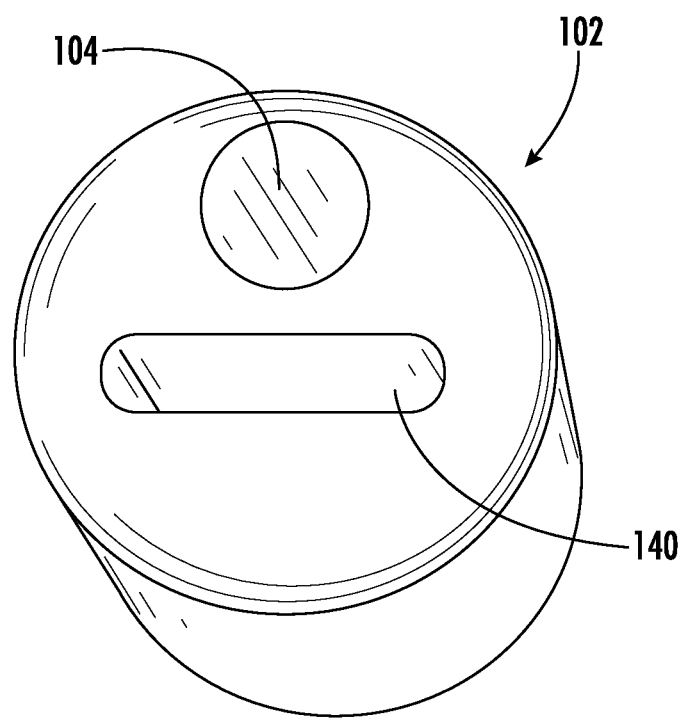
FIG. 17 is a profile view of the dorsal base of a male urinary incontinence device, in accordance with one embodiment.

According to one embodiment, and as shown in FIG. 17, the dorsal base 102 may include a dorsal base aperture 104 and a dorsal base receiver 140, wherein the dorsal base aperture 104 may be offset from the central longitudinal axis of the dorsal base 102 to accommodate the dorsal base receiver 140. Similarly, the dorsal base receiver 140 may extend partially or completely through the dorsal base 102.

Figure 18:
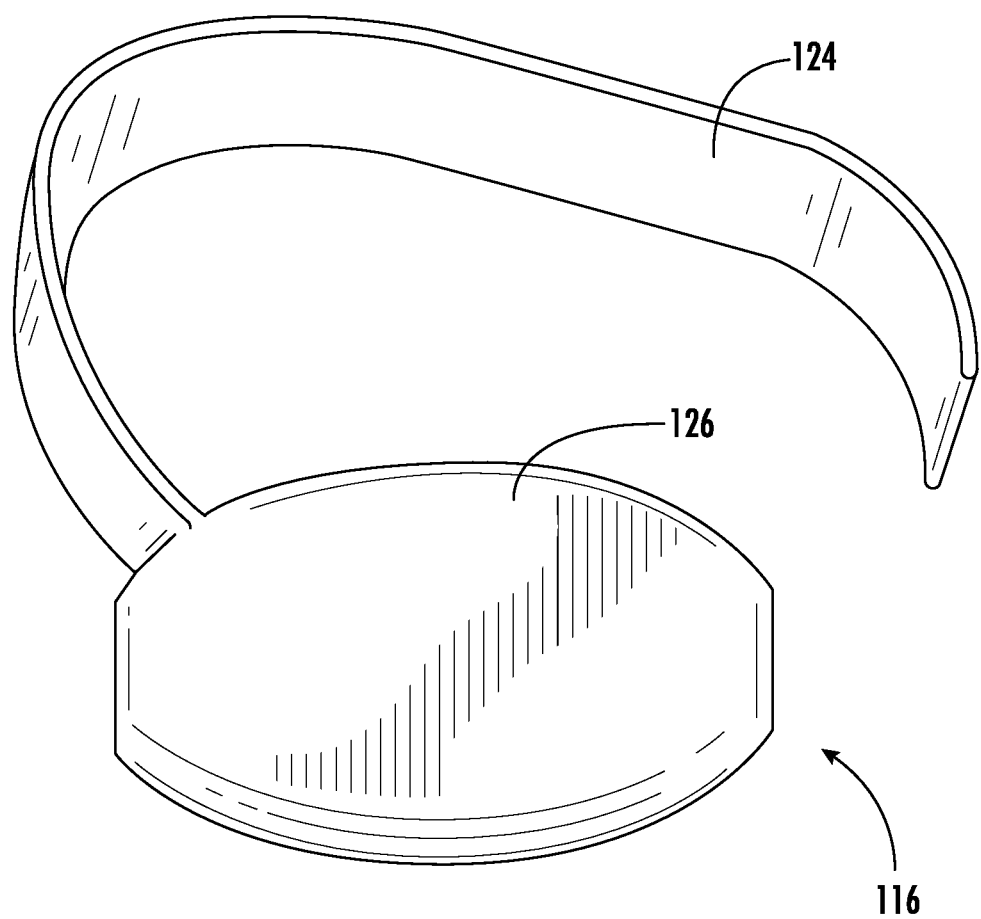
FIG. 18 is a front view of the ventral base of a male urinary incontinence device, in accordance with one embodiment.
Figure 19:
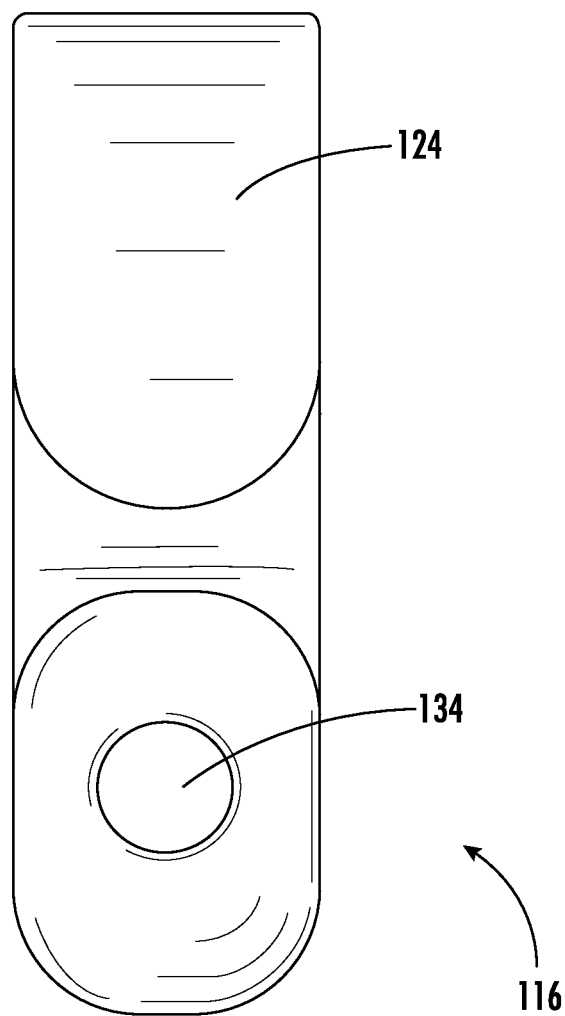
FIG. 19 is a profile view of the ventral base of a male urinary incontinence device, in accordance with one embodiment.
Figure 20:
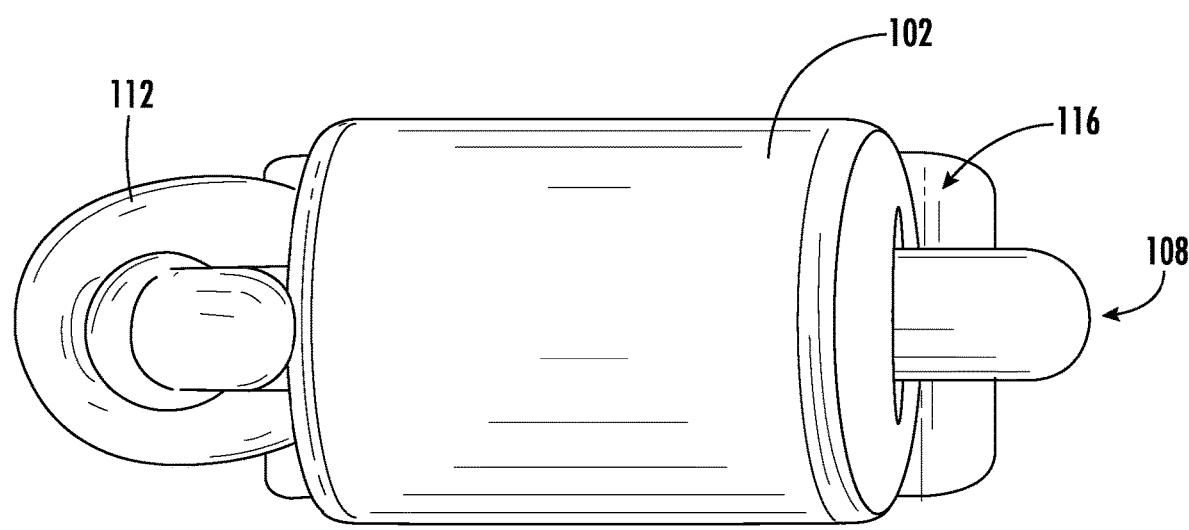
FIG. 20 is a top view of a male urinary incontinence device, in accordance with one embodiment.
Figure 21:
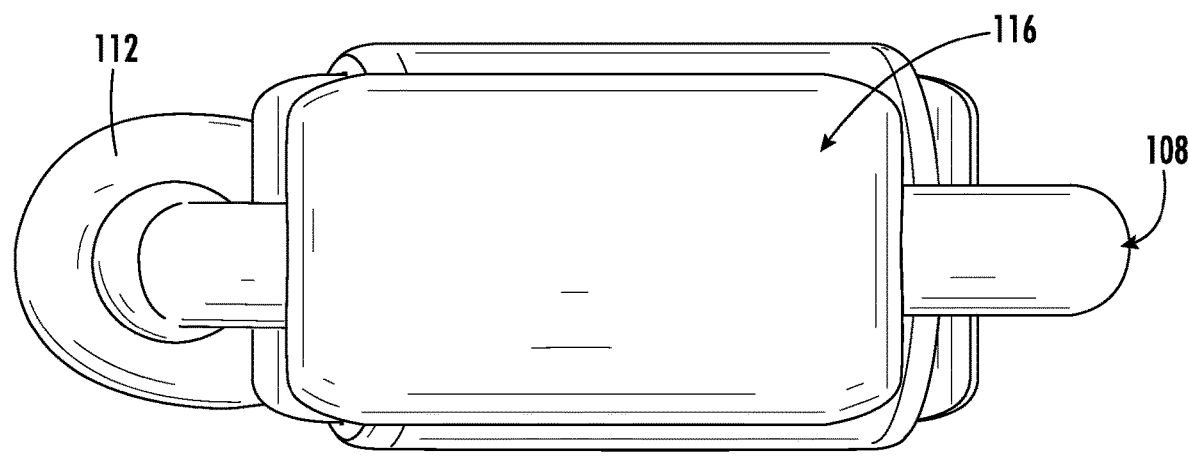
FIG. 21 is a bottom view of a male urinary incontinence device, in accordance with one embodiment.
Figure 22:
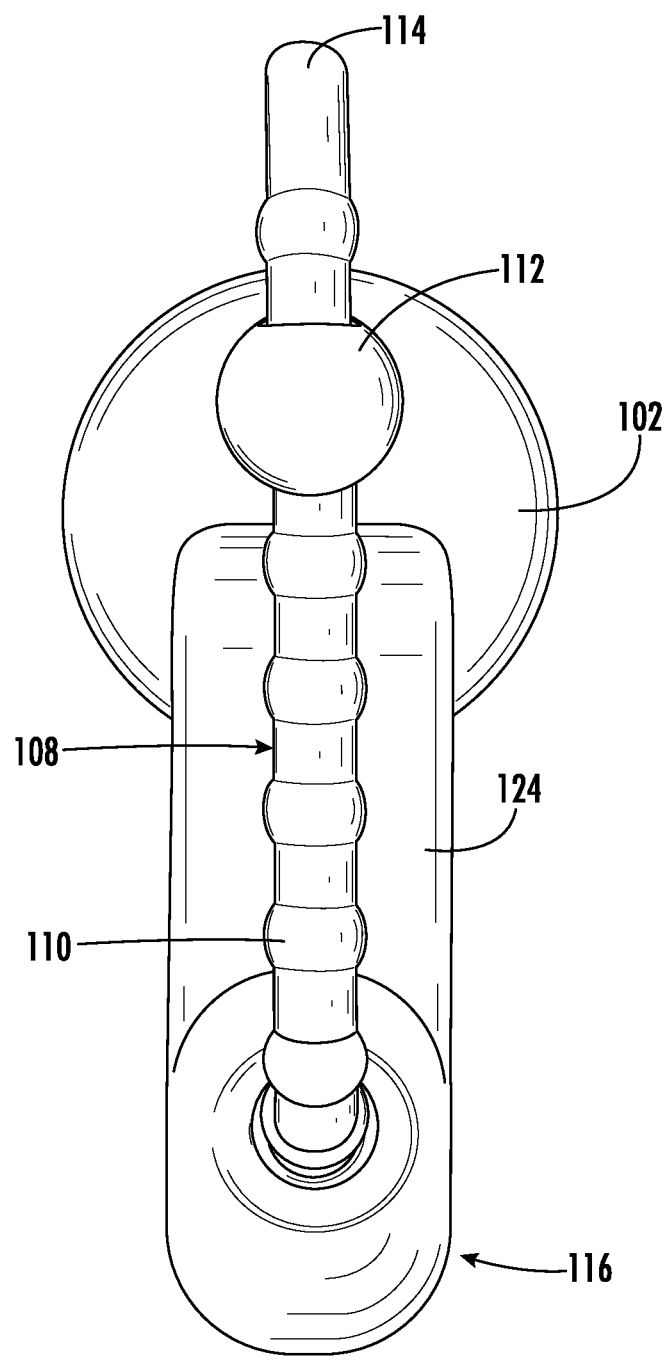
FIG. 22 is a profile view of a male urinary incontinence device, in accordance with one embodiment.
Figure 23:
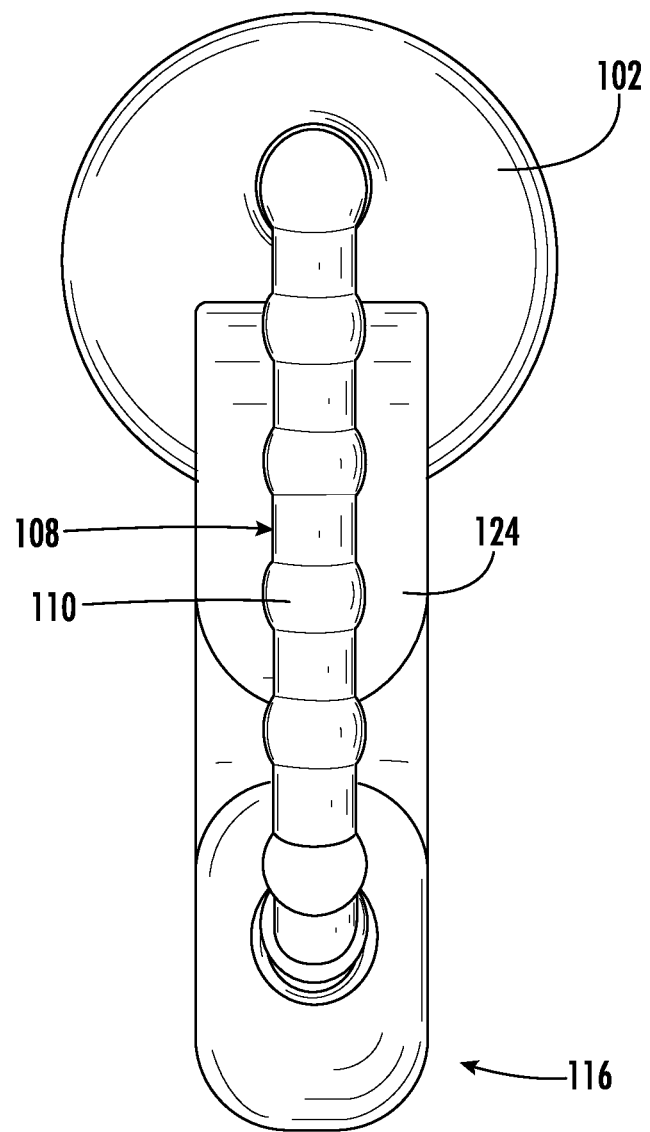
FIG. 23 is a profile view of a male urinary incontinence device, in accordance with one embodiment.

According to one embodiment and as shown in FIG. 18, the lateral ventral flange 124 may lack a lateral ventral notch 130 where the lateral ventral flange 124 may be secured to the dorsal base 102 by its insertion into the dorsal base receiver 140. As shown in FIG. 13, for example, the lateral ventral flange 124 may be inserted through the dorsal base receiver 140 such that a portion of the lateral ventral flange 124 may extend outward through the opposing opening of the dorsal base receiver 140.

Figure 16:
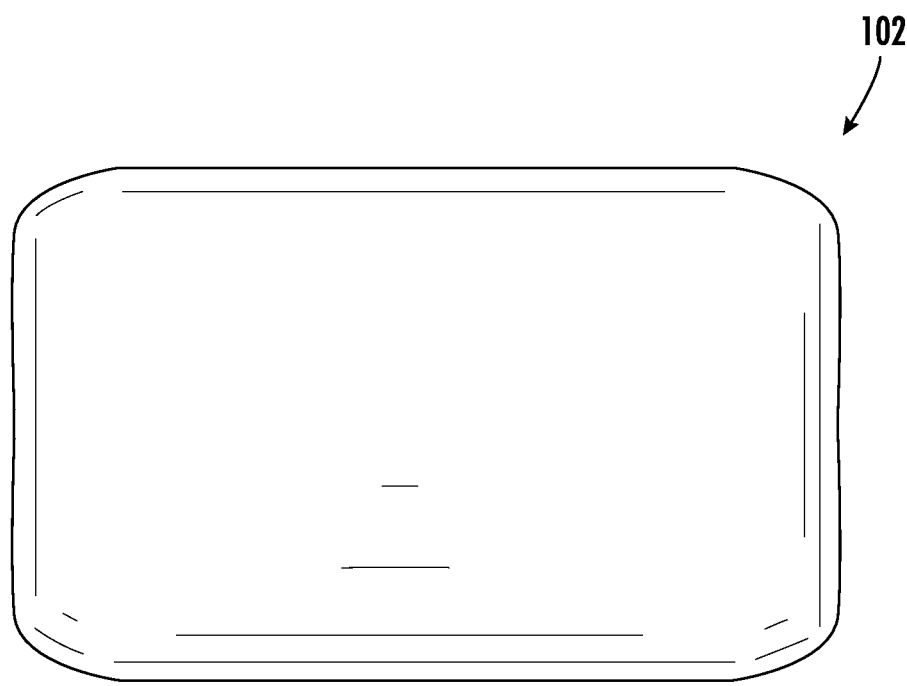
FIG. 16 is a front view of the dorsal base of a male urinary incontinence device, in accordance with one embodiment.

It will be appreciated by one of ordinary skill in the art, and as shown, for example, in FIG. 16, the dorsal base 102 may lack the plurality of dorsal base protuberances 106.

According to one embodiment, all or a portion of the individual components may be composed of nonporous materials, including materials capable of being subjected to extreme temperatures without alternating the material's mechanical properties. For example, the components may be composed of silicon, plastic, polypropylene, or a composite thereof or other similar materials. Such properties allow the individual components to be cleaned or sanitized in, for example, boiling or near-boiling water or in cleaning solutions.

While the present invention has been shown and described in accordance with several preferred and practical embodiments, it is recognized that departures from the instant disclosure are contemplated within the spirit and scope of the present invention.

What is claimed is:

1. A male urinary incontinence device comprising:
   a circumferential band having a securing end, an elongated portion, and a receiving end, wherein the elongated portion is positioned between the securing end and the receiving end;
   the receiving end including a receiving aperture, the receiving aperture sized for receipt of the securing end, and the elongated portion extends through the receiving aperture;
   a ventral base having a ventral base aperture and a lateral ventral flange;
   the ventral base aperture sized for receipt of the securing end, and the elongated portion of the circumferential band extends through the ventral base aperture;
   a dorsal base having a dorsal base aperture and a dorsal base receiver;
   the dorsal base aperture sized for receipt of the securing end, and the elongated portion of the circumferential band extends through the dorsal base aperture; and
   wherein the dorsal base receiver extends through the dorsal base and receives the lateral ventral flange.

2. The male urinary incontinence device of claim 1, wherein the dorsal base includes a central axis located along a central longitudinal axis of the dorsal base;
   the dorsal base receiver being positioned offset from and parallel to the central axis.

3. The male urinary incontinence device of claim 2, wherein the dorsal base aperture is positioned offset from and parallel to the central axis.

4. The male urinary incontinence device of claim 1, wherein a plurality of protuberances are located on an exterior surface of the elongated portion of the circumferential band.

5. The male urinary incontinence device of claim 1, wherein the circumferential band, the ventral base, and the dorsal base are each composed of one or more nonporous materials.

6. A male urinary incontinence device comprising:
   a circumferential band, the circumferential band having a securing end, an elongated portion, and a receiving end;
   the receiving end including a receiving aperture sized for receipt of the securing end, and the elongated portion extends through the receiving aperture;
   a dorsal base including a dorsal base aperture and a dorsal base receiver, the dorsal base aperture sized for receipt of the securing end, and the elongated portion of the circumferential band extends through the dorsal base aperture;
   a ventral base having a lower ventral bar, a ventral base aperture, and at least one lateral ventral flange, wherein the ventral base aperture is sized for receipt of the securing end, and the elongated portion of the circumferential band extends through the ventral base aperture; and
   wherein the dorsal base receiver extends through the dorsal base and receives the at least one lateral ventral flange.

7. The male urinary incontinence device of claim 6, wherein a plurality of protuberances are located on an exterior surface of the circumferential band.

8. The male urinary incontinence device of claim 6, wherein the dorsal base includes a central axis located along a central longitudinal axis of the dorsal base;

the dorsal base aperture positioned parallel to the central axis.

9. The male urinary incontinence device of claim 6, wherein the dorsal base receiver is positioned parallel to the dorsal base aperture.

10. The male urinary incontinence device of claim 6, wherein the circumferential band, the ventral base, and the dorsal base are each composed of one or more nonporous materials.

11. A male urinary incontinence device comprising:
- a circumferential band having a securing end, an elongated portion, and a receiving end, wherein the elongated portion is positioned between the securing end and the receiving end;
- the receiving end including a receiving aperture, the receiving aperture having an outer diameter, an inner diameter, and an inner aperture, wherein the receiving aperture is sized for receipt of the receiving end, and the elongated portion of the circumferential band extends through the receiving aperture;
- the elongated portion including a plurality of protuberances located on an exterior surface of the circumferential band;
- a dorsal base having a dorsal base aperture and a dorsal base receiver;
- the dorsal base aperture sized for receipt of the securing end, and the elongated portion of the circumferential band extends through the dorsal base aperture;
- a ventral base having a ventral base aperture sized for receipt of the securing end, and the elongated portion of the circumferential band extends through the ventral base aperture, and at least one lateral ventral flange; and
- wherein the dorsal base receiver extends through the dorsal base and receives the at least one lateral ventral flange.

12. The male urinary incontinence device of claim 11, wherein each of the plurality of protuberances has a maximum diameter that is greater than a diameter of the inner aperture.

13. The male urinary incontinence device of claim 11, wherein the dorsal base receiver is positioned parallel to the dorsal base aperture.

14. The male urinary incontinence device of claim 11, wherein the circumferential band, the ventral base, and the dorsal base are each composed of one or more nonporous materials.

* * * * *